US008871993B2

(12) United States Patent
Buus et al.

(10) Patent No.: US 8,871,993 B2
(45) Date of Patent: Oct. 28, 2014

(54) PERMEABLE PRESSURE SENSITIVE ADHESIVE

(75) Inventors: Hasse Buus, Humlebæk (DK); Tom Bjarnum Kongebo, Humlebæk (DK); Astrid Carlsen, Helsingør (DK)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 13/701,514

(22) PCT Filed: Jun. 17, 2011

(86) PCT No.: PCT/DK2011/050220
§ 371 (c)(1),
(2), (4) Date: Dec. 3, 2012

(87) PCT Pub. No.: WO2011/157278
PCT Pub. Date: Dec. 22, 2011

(65) Prior Publication Data
US 2013/0090588 A1 Apr. 11, 2013

(30) Foreign Application Priority Data

Jun. 18, 2010 (DK) .................................. 2010 70269
Dec. 22, 2010 (DK) .................................. 2010 70571

(51) Int. Cl.
| *A61F 5/443* | (2006.01) |
| *A61F 13/02* | (2006.01) |
| *C08L 23/06* | (2006.01) |
| *C08L 23/22* | (2006.01) |
| *C08L 53/02* | (2006.01) |
| *A61L 15/58* | (2006.01) |
| *A61L 24/04* | (2006.01) |

(52) U.S. Cl.
CPC ............. *A61F 13/0253* (2013.01); *A61F 5/443* (2013.01); *A61L 15/585* (2013.01); *A61L 24/043* (2013.01)
USPC .............. 602/54; 523/105; 604/332; 606/214

(58) Field of Classification Search
None
See application file for complete search history.

(56) References Cited

U.S. PATENT DOCUMENTS

| 3,282,881 | A | * | 11/1966 | Flanagan ........................ 525/185 |
| 3,322,706 | A | * | 5/1967 | McAninch ........................ 524/69 |
| 3,644,252 | A | * | 2/1972 | Shenfeld et al. .............. 524/522 |
| 3,972,328 | A | * | 8/1976 | Chen ................................ 602/56 |
| 4,172,939 | A | * | 10/1979 | Hoh ................................ 528/392 |
| 4,551,490 | A | * | 11/1985 | Doyle et al. ..................... 524/22 |
| 4,855,335 | A | * | 8/1989 | Neperud ........................ 523/111 |
| 5,054,488 | A | | 10/1991 | Muz |
| 5,133,821 | A | | 7/1992 | Jensen |
| 5,458,124 | A | | 10/1995 | Stanko et al. |
| 5,849,843 | A | * | 12/1998 | Laurin et al. ..................... 525/66 |
| 6,372,951 | B1 | | 4/2002 | Ter-Ovanesyan et al. |
| 6,385,473 | B1 | | 5/2002 | Haines et al. |
| 6,716,527 | B1 | * | 4/2004 | Czmok et al. .................. 428/403 |
| 6,773,772 | B2 | * | 8/2004 | Shinozaki et al. ............ 428/32.6 |
| 7,119,155 | B2 | * | 10/2006 | Chow et al. .................... 526/172 |
| 7,279,536 | B2 | * | 10/2007 | Brant et al. .................... 526/160 |
| 2003/0009097 | A1 | | 1/2003 | Sheraton et al. |
| 2013/0220667 | A1 | * | 8/2013 | Millan Perez et al. .. 174/120 SR |

FOREIGN PATENT DOCUMENTS

| EP | 0264299 | 4/1988 |
| WO | 9911302 | 3/1999 |
| WO | 9959465 | 11/1999 |
| WO | 02066087 | 8/2002 |
| WO | 03065926 | 8/2003 |
| WO | 2007082538 | 7/2007 |
| WO | 2009006901 | 1/2009 |
| WO | WO 2009006901 A1 * | 1/2009 | ............. C09J 123/08 |

* cited by examiner

*Primary Examiner* — James J Seidleck
*Assistant Examiner* — Peter A Salamon
(74) *Attorney, Agent, or Firm* — Coloplast Corp., Coloplast A/S; Nick Baumann

(57) ABSTRACT

The present invention relates to a pressure sensitive adhesive composition for skin application. The adhesive composition comprises 10-50% (w/w) based on the total adhesive composition of a polar part; 10-50% (w/w) based on the total adhesive composition of an apolar part; and 0-60% (w/w) based on the total adhesive composition of hydrocolloid.

30 Claims, No Drawings

PERMEABLE PRESSURE SENSITIVE ADHESIVE

FIELD OF THE INVENTION

The present invention relates to a pressure sensitive, hot melt processable adhesive composition comprising a polar part, an apolar part and hydrocolloids and a medical device comprising the adhesive composition according to the invention.

BACKGROUND OF THE INVENTION

For a long time, pressure sensitive adhesives have been used for attaching medical devices, such as ostomy appliances, dressings (including wound dressings), wound drainage bandages, devices for collecting urine, orthoses and prostheses to the skin.

In connection with surgery for a number of diseases in the gastro-intestinal tract a consequence in many cases is, that the colon, the ileum or the urethra has been exposed surgically. The patient is left with an abdominal stoma and the effluents or waste products of the body, which are conveyed through these organs, are discharged through the artificial orifice or opening and are collected in a collection bag. The bag is usually adhered to the skin by means of an adhesive wafer or plate having an inlet opening for accommodating the stoma.

Traditionally, pressure sensitive adhesives used for an ostomy appliance are relatively hard hydrocolloid adhesives with a high tendency to strip the skin. The reason for this is that the adhesive should be able to withstand body movements and have a hydrocolloid content that is high enough to absorb moisture and sweat from the skin.

Optimal adhesives for an ostomy base plate have to perform under a variety of conditions, such as differences in fluidity and amount of stoma exudates, body shape, skin firmness, skin irregularities, activity and perspiration level, and of course the variation in the end-user's preferred changing pattern of the device.

An adhesive suitable for these applications should have a composition that is skin friendly in order to facilitate frequent changing. Furthermore, the adhesive should have a high moist absorption level and a high erosion resistance in order not to expose the skin to exudates from the stoma. Moreover, the adhesive should be flexible enough to adapt to the contours of the skin.

Adhesives such as described in WO 99/11302 perform well during perspiration. These adhesives typically have a high level of plasticity so that the adhesive will flow well to the skin after application. These adhesives have the disadvantage that they disintegrate during the contact with effluents from a stoma or a wound. The low tack of these adhesives makes the performance of the appliance sensible to how the user applies the product and usually requires that the user doesn't move around too much in a period immediately after application to avoid the adhesive from falling off. These types of adhesives are most often not flexible enough to fit well to hernias, skin folds and scars in the peristomal area. A poor fit to the skin will decrease the contact area between the appliance and the skin and greatly increase the risk of leakage. To make these adhesives more flexible the thickness could be lowered. This, however, will markedly reduce the adhesives overall capacity for absorbing perspiration, and because of the low tack, the sensibility of the application procedure will increase. Overall, these types of adhesives will not perform well in a flexible design.

Adhesives, such as described in U.S. Pat. No. 4,551,490 and WO 2007/082538, are usually more tacky and cohesive in the continuous phase compared to the adhesives described in WO 99/11302. This makes the continuous phase less prone to disintegration during the swelling of the hydrocolloids. The drawback of these adhesives is that the increased cohesiveness will reduce the absorption rate. Because the adhesives have a deficiency in plastic deformation, excessive swelling of the adhesives during contact with exudates will make them lose contact with the skin, resulting in the skin being exposed.

Therefore, these types of adhesives have lower initial overall water absorption. In order to perform in hot areas and/or on people with a high perspiration level, a certain amount of resin usually needs to be added. This will make the adhesives more aggressive and less skin friendly and therefore less suited for wear-times less than 48 hours.

An alternative to the absorbing adhesives described above is a liquid impermeable, moisture permeable adhesive such as polyurethane, silicone and polyacrylate. These adhesives are usually very soft and flexible and adapt well to skin fold and scars in the peristomal skin. However, they lack the ability of ion exchanging whereby the pH value of the skin is not maintained. The adhesives are often too soft to withstand contact with extrudes with low surface tension.

It has now surprisingly been found that by utilizing a soft permeable agent in combination with traditional hydrocolloid adhesives, such as described in WO 99/11302, an adhesive composition can be produced that is soft and tacky enough to adapt to skin contours such as scars and folds. Furthermore, it has improved erosion resistance, without compromising the moist absorption and ease of removal, nor introducing other possible adverse effects.

SUMMARY OF THE INVENTION

The present invention relates to a pressure sensitive adhesive composition for skin application. The adhesive composition comprises 10-50% (w/w) based on the total adhesive composition of a polar part; 10-50% (w/w) based on the total adhesive composition of an apolar part; and 0-60% (w/w) based on the total adhesive composition of hydrocolloid.

DETAILED DESCRIPTION OF THE INVENTION

In one embodiment of the present invention, the pressure sensitive adhesive composition for skin application comprising 10-50% (w/w) based on the total adhesive composition of a polar part;
10-50% (w/w) based on the total adhesive composition of an apolar part; and
0-60% (w/w) based on the total adhesive composition of hydrocolloid(s), wherein
the polar part comprising polar polyethylene copolymer(s) and polar oil; and
the apolar part comprising polyisobutylene and styrene block copolymer or butyl rubber.

Polymers that may be used in the practice of the invention will generally be copolymers of ethylene and a polar monomer. The copolymers typically comprise less than about 70% ethylene, have water vapour transmission of more than 50 $g/m^2/day$ and a melt flow index of less than 2 g/10 min (190° C./21.1N). The melt flow index can be measured by the methods given in ISO 1133 and ASTM D1238. Examples of such polymers are copolymers of ethylene and vinyl acetate and copolymers of ethylene and butyl acrylate. Particularly preferred are ethylene and vinyl acetate copolymers with more than about 40% (w/w) vinyl acetate, a melt flow index of less than 2 g/10 min (190° C./21.1N) and a water vapour transmission of more than 50 g/m²/day for a 150 μm sheet when measured according to the Moisture Vapour Transmission Rate (MVTR) test method.

Combining an apolar and a polar phase in the continuous phase of a hydrocolloid adhesive makes it possible to optimise properties by adjusting softness, plasticity/elasticity and adhesion in either phase and thereby to a much larger extent produce adhesives with improved properties with respect to skin friendliness, cold flow, erosion, residues upon removal and moist handling. As the polar phase also increases the permeability of the adhesives significantly it is possible to combine the adhesive with a permeable backing and create a device that has a lower thickness than the usual hydrocolloid adhesives without compromising the performance during perspiration and avoid adverse effects such as skin maceration and fungus infections.

For the end-user the increased tack of the adhesives will make performance less sensitive to errors performed during application and thereby preventing leakages. The increased softness of the adhesives and the reduced thickness will result in a device that is more flexible and pliable and will fit body contours and movements. The higher erosion resistance will reduce/prevent skin contact with aggressive body exudates that are a major cause of skin problems. High water absorption and a low level of skin stripping improve the health of the skin, and increase resistance to degradation and infections. Overall, end-users will experience increased safety and increased skin health during use, as well as achieving improved comfort and moveability.

Combining thermoplastic materials that are highly permeable and non-polar materials (continuous phase) respectively, could cause stability issues due to phase separation or migration. However, ageing studies have proven that these compositions according to the invention have the desired stability with respect to water absorption, adhesion and rheological properties. Dynamic mechanical analysis shows uniform curves of IG*I and tan(δ) with a combined rheological expression of both the apolar and the highly permeable part.

In one embodiment of the present invention, the polar part comprising a polar plasticizing oil or a combination of polar plasticizing oils in the content of above 10% (w/w) of said polar part, the content of the polyethylene copolymer(s) is 10-50% (w/w) of said polar part, and at least one polar polyethylene copolymer has a melt flow index below 2 g/10 min (190° C./21.1N).

In another embodiment of the present invention, the polar part comprises a polar plasticizing oil or a combination of polar plasticizing oils in the content of above 10% (w/w) of said polar part, the content of the polyethylene copolymer(s) is 10-50% (w/w) of said polar part, and the polar polyethylene copolymer(s) has a melt flow index below 2 g/10 min (190° C./21.1N).

In an embodiment of the invention, the final adhesive composition in continuous form exhibits a moisture vapour transmission rate of at least 400 g/m²/24 hours, preferably at least 650 g/m²/24 hours for a 500 μm sheet when measured according to the MVTR test method.

The primary polymers used in the adhesive composition are polyethylene copolymers. The copolymer should contain a considerable amount of a polar component to get high water permeability.

In one embodiment of the invention, the polar polyethylene copolymer is selected from the group consisting of ethylene vinyl acetate, ethylene vinyl acetate carbon monoxide, ethylene butyl acetate, ethylene vinyl alcohol, ethylene butyl acrylate, ethylene butyl acrylate carbon monoxide, and combinations thereof.

The polar polyethylene copolymer is preferably ethylene vinyl acetate.

By polar polymers is meant polymers with water transmission above 50 g/m²/day for a 150 μm film when measured according to the MVTR test method.

One object of this invention is to provide a water permeable adhesive, i.e. an adhesive, which can be hot-melt processed and which at normal use conditions can be removed without leaving significant residues.

In an embodiment of the invention, the ethylene vinyl acetate has a content of at least 40% (w/w) vinyl acetate preferably with 40-80% (w/w) vinyl acetate.

Preferably, the polar polyethylene copolymers used in the adhesive should have a molecular structure at a level that results in a melt flow index (MFI) below 2 g/10 min (190° C./21.1N). The melt flow index can be measured by the methods given in ISO 1133 and ASTM D1238.

The advantage of using a polymer with high molecular weight and low MFI is that the high molecular weight polymer can ensure a sufficient high cohesive strength to the adhesive.

By the content of the final adhesive is meant the percentage in weight of the ingredient in relation to the total weight of the ingredients used in the adhesive composition.

In an embodiment of the invention, the polar polyethylene copolymer(s) has a molecular weight above 250,000 g/mol.

In one embodiment of the present invention, the adhesive composition comprising a polar plasticizing oil or a combination of polar plasticizing oils in the content of 5-40% (w/w) of the final adhesive.

In one embodiment of the present invention, the adhesive composition comprising a polar plasticizing oil, wherein the polar plasticizing oil is selected from the group of liquid rosin derivatives, aromatic olefin oligomers, vegetable and animal oils and derivatives. Preferable polar oils are esters, ethers and glycols.

Particularly preferable oils are poly propylene oxides such as alpha-butoxy-polyoxypropylene or polypropylene glycol. Polypropylene oxide oil contributes to a high permeability of the adhesive composition.

According to an embodiment of the invention, the ration of polar polyethylene copolymer and polar oil is between 1:1 and 1:4.

Some of the adhesive compositions according to the invention contain a minor amount of additional polar polymer in the adhesive besides the main polymer adding cohesion. This or these additional polymers are added to give tack. These additional polymers are optional and not necessary for all purposes.

In one embodiment of the invention, the adhesive composition further comprises a low molecular weight polar polymer, that is MFI >2.

According to an embodiment of the invention, the polyisobutylene has a molecular weight of below 100,000 g/mol, preferably 40,000-60,000 g/mol. Examples of such polyisobutylenes are Oppanol B10 SFN and Oppanol B12 SFN with molecular weights of 40,000 and 60,000 g/mole respectively.

The block copolymer may be a copolymer comprising a block of a relatively hard polymer which may form physical cross-linking and a block of a softer polymer. The constituents of the block copolymer may be the same as are conventionally used for styrene block copolymers such as polystyrene-block-polybutadiene-block-polystyrene (SBS), polystyrene-block-polyisoprene-block-polystyrene (SIS) or polystyrene-block-poly(ethylene/butylene)-block-polystyrene (SEBS) copolymer, for example styrene and butadiene, isoprene or ethylenebutylene copolymers. The preferred copolymer is a styrene-isoprene copolymer and is preferably a mixture of styrene-isoprene-styrene and styrene-isoprene copolymer.

In one embodiment of the invention, the styrene block copolymer is a styrene-isoprene-styrene block copolymer.

An elastomeric polymer such as butyl rubber or a high molecular weight polyisobutylene may be blended into the apolar phase. The butyl rubber may be used in the viscosity average molecular weight range of about 200,000 to about 600,000 g/mol. The high molecular weight butyl rubber may be added in an amount suitable to modify various properties of the final formulation.

According to an embodiment of the invention, the butyl rubber has an average molecular weight of 200,000 to 600,000 g/mol.

The adhesive composition may comprise styrene block copolymer, butyl rubber and polyisobutylene.

Additional components may be added to the composition such as tackifier resin, plasticisers and wax. The additional components can be used to control the properties of the polar phase or the apolar phase of the adhesive. This is possible by selecting the components that are fully or predominantly compatible with either phase.

In one embodiment of the invention, the adhesive composition further comprises a tackifier resin such as natural, modified or synthetic resins preferably polar resins such as rosins, rosin esters, hydrogenated rosins, hydrogenated rosin esters, and derivatives of such polar resins or pure aromatic monomer resins.

Tackifier resins can be added to control tack in the adhesive, that is they reduce moduli and increase glass transition temperature.

In another embodiment of the invention, the adhesive composition comprises an apolar resin compatible with the apolar part of the adhesive such as hydrogenated hydrocarbon resins.

The content of the tackifier resin is 0-20% (w/w) of the final adhesive. Preferably the adhesive is substantially free of resin. When the adhesive composition contains resin, the content of the tackifier resin is preferably 0.1-20% (w/w) of the final adhesive.

In one embodiment of the invention, the adhesive composition further comprises an additional plasticiser selected from the group of mineral oil, citrate oil, paraffin oil, phatalic acid esters, adepic acid esters (e.g. dioctyl adipate (DOA)), and liquid or solid resin.

In another embodiment of the invention, the adhesive composition further comprises a polyethylene wax.

Other ingredients may be added for auxiliary benefits. This could be antioxidants and stabilisers, fillers for rheology modification or active components like vitamin E or ibuprofen.

In another embodiment of the invention, the adhesive composition further comprises other ingredients selected from the group of antioxidants, stabilisers, fillers, pigments, flow modifiers, and active ingredients.

In one preferred embodiment of the invention, the adhesive composition comprises polar active ingredients.

According to an embodiment of the invention, the composition comprises absorbing particles such as hydrocolloid.

As with traditional hydrocolloid adhesives and pastes, most liquid absorbing polymeric particles can be used, including microcolloids.

More particularly, the hydrocolloids may be guar gum, locust bean gum (LBG), pectin, alginates, potato starch, gelatine, xanthan, gum karaya; cellulose derivatives (e.g. salts of carboxymethylcellulose such as sodiumcarboxymethylcellulose, methylcellulose, hydroxyethyl cellulose and hydroxypropylmethylcellulose), sodium starch glycolate, polyvinylalcohol and/or polyethylene glycol.

In one embodiment of the invention, the content of hydrocolloid is 30-50% (w/w) of the total composition.

Microcolloid particles are well known in the art, for example from International Publication No. WO 02/066087, which discloses adhesive compositions comprising microcolloid particles. The microcolloid particles may have a particle size of less than 20 microns.

In one embodiment of the invention, the content of the polar part is 20-40% (w/w) of the total adhesive composition.

According to one embodiment of the invention, the content of the apolar part is 20-40% (w/w) of the total adhesive composition.

According to an embodiment of the invention, the ration of the content of the polar part and the apolar part is between 1:4 and 4:1, preferably between 2:3 and 3:2.

The invention also relates to medical devices comprising a pressure sensitive adhesive composition as described above.

The medical device comprising an adhesive composition according to the invention may be an ostomy appliance, a dressing, a skin protective bandage, a device for collecting urine, an orthose or a prosthese, e.g. a breast prosthesis, a faecal management device, and electronic device such as a measuring instrument or a power source, such as a battery.

The medical device may also be a tape (e.g. an elastic tape or film), or a dressing or a bandage, for securing a medical device, or a part of the medical device to the skin, or for sealing around a medical device attached to the skin.

The medical device may in its simplest construction be an adhesive construction comprising a layer of the pressure sensitive adhesive composition according to the invention and a backing layer.

The backing layer is suitably elastic (has a low modulus), enabling the adhesive construction to conform to the skin movement and provide comfort when using it.

In a preferred embodiment of the invention, the backing material has a structured surface to improve the adhesion between the adhesive and the backing material.

Particularly preferred are backing materials where the molted adhesive can penetrate and create mechanical interlocking with for example Non Woven and non-woven film laminates.

The thickness of the backing layer used according to the invention is dependent on the type of backing used. For polymer films, such as polyurethane films, the overall thickness may be between 10 to 100 µm, preferably between 10 to 50 µm, most preferred about 30 µm.

In one embodiment of the invention, the backing layer is non-vapour permeable.

In another embodiment of the invention, the backing layer is water vapour permeable and has a moisture vapour transmission rate above 500 $g/m^2/24$ h. In this case the adhesive construction of the invention may provide a good moisture transmission rate and is able to transport a large quantity of moisture through the construction and away from the skin. Both the chemical composition and physical construction of the adhesive layer, and the chemical and physical construction of the backing layer affect the water vapour permeability. With regard to the physical construction, the backing layer may be continuous (no holes, perforations, indentations, no added particles or fibres affecting the water vapour permeability) or discontinuous (it has holes, perforations, indentations, added particles or fibres affecting the water vapour permeability).

The moisture vapour transmission rate of the backing layer is suitably above 500 g/m$^2$/24 h, most preferably above 1,000 g/m$^2$/24 h, even more preferred above 3,000 and most preferred above 10,000.

In another embodiment of the invention, a layered adhesive construction comprises a backing layer and at least one layer of a pressure sensitive adhesive composition according to the invention.

The adhesive according to the invention may be foamed into foamed adhesive in a number of ways, either chemically or mechanically.

Chemical blowing agents or other materials added to the adhesive formula itself may generate gas bubbles by a variety of mechanisms. These mechanisms include but are not limited to chemical reaction, physical changes, thermal decomposition or chemical degradation, leaching of a dispersed phase, volatilisation of low boiling materials or by a combination of these methods.

Any of the commercially known chemical blowing agents may be used. The chemical blowing agents are suitably nontoxic, skin friendly and environmentally safe, both before and after decomposition.

The amount of chemical blowing agent to be added to the adhesive mixture may range from about 0.01% up to about 90% by weight, with a practical range including about 1% up to about 20% by weight. The amount of gas to be added may be determined by measuring the amount of gas generated from a candidate mixture and calculating the amount of foaming required for the final product, tempered by experience of the amount of gas lost to atmosphere during the foaming process.

Another method for creating a foamed adhesive of the invention is a method where a mechanical process is used to add a physical blowing agent, similar to whipping the adhesive mass into froth, thus creating a foamed structure. Many processes are possible including processes involving incorporation of air, nitrogen, carbon dioxide, or other gases or low boiling point volatile liquids during the manufacturing process for the adhesive.

According to a further embodiment, the invention relates to a medical device such as a thin adhesive dressing, wherein the thickness of the adhesive layer is between 50 and 250 μm where it is thickest. The adhesive layer may thus be of varying thickness or it may have a uniform thickness selected from values between 50 and 250 μm.

A dressing of the invention may in a preferred embodiment comprise an absorbing pad for the uptake of body fluids, especially wound exudates, so as to enable the wound dressing to keep a constant moist environment over the wound site and at the same time avoid maceration of the skin surrounding the wound.

A dressing of the invention is optionally covered in part or fully by one or more release liners or cover films that are to be removed before or during application. A protective cover or release liner may for instance be siliconised paper. It does not need to have the same contour as the dressing and a number of dressings may be attached to a larger sheet of protective cover. The release liner may be of any material known to be useful as a release liner for medical devices.

The protective cover is not present during the use of the dressing of the invention and is therefore not an essential part of the invention. Furthermore, the dressing of the invention may comprise one or more "non touch" grip(s) known per se for applying the dressing to the skin without touching the adhesive layer. Such a non-touch grip is not present after application of the dressing. For larger dressings it is suitable to have 2 or 3 or even 4 "non-touch" grips.

Flexibility in the adhesive part of a medical device is often achieved by device design, such as bevelling or patterning in the adhesive.

A dressing or adhesive sheet of the invention may have bevelled edges in order to reduce the risk of "rolling-up" the edge of the dressing, thereby reducing the wear-time. A bevelling may be carried out discontinuously or continuously in a manner known per se e.g. as disclosed in EP Patent No. 0 264 299 or U.S. Pat. No. 5,133,821.

In another aspect, the invention relates to a wafer for an ostomy appliance comprising an adhesive construction as described above.

An ostomy appliance of the invention may be in the form of a wafer forming part of a two-piece appliance or in the form of a one-piece appliance comprising a collecting bag for collecting the material emerging from the stoma. A separate collecting bag may be attached to the wafer by any manner known per se, e.g. through mechanical coupling using a coupling ring or through use of adhesive flanges.

A wafer for an ostomy appliance of the invention also typically comprises a water vapour permeable and water impervious reinforcement material and a release liner as discussed above.

An ostomy appliance of the invention may be produced in a manner known per se from materials conventionally used for the preparation of ostomy appliances.

Devices with advantageous properties may be obtained using the permeable adhesives of the invention in laminated constructions.

In one embodiment of the invention, the construction further comprises at least one layer of a water absorbing adhesive.

Devices with very good adhesion under extreme conditions, for example high moisture load from heavy sweating, may be obtained by placing a layer, preferably a thin layer, of permeable but non-absorbing adhesive (no hydrophilic fillers) of the invention between a water absorbing adhesive and the skin. In this way, good adhesive power can be maintained even after the adhesive has absorbed a considerable amount of water.

It is a particular advantage to use the absorbing adhesive constructions according to the invention in connection with ostomy appliances, because the adhesive can be made resistant to the aggressive fluids from the stoma, without sacrificing too much water absorption. Hence, it is possible to make devices which shield the skin efficiently from the corrosive stoma fluids and at the same time provide a healthy non occlusive micro environment between the adhesive and the skin.

In a further embodiment, the invention relates to prosthesis of the type to be adhered to the skin of the user, such as a breast prosthesis comprising an adhesive construction according to the invention.

The invention also relates to a urine collecting device comprising an adhesive construction as described above.

Urine collecting devices according to the invention may be in the form of urisheaths.

As mentioned above, the medical device may also be a medical tape e.g. for securing a device or a part of a device to the skin.

The medical device according to the invention may also be a measuring instrument or a therapeutic instrument, which is attached to the skin, such as devices useful for measuring ECG (Electro CardioGraphy), EMG (Electro MyoGraphy), EEG (Electro EncephaloGraphy), blood glucose, pulse, blood pressure, pH, and oxygen.

Such measuring instruments are known in the art and they are usually attached to the skin by a pressure sensitive adhesive.

Examples of such devices are described in e.g. International Publication No. WO 03/065926, U.S. Pat. No. 5,054,488, U.S. Pat. No. 5,458,124, U.S. Pat. No. 6,372,951, U.S. Pat. No. 6,385,473, International Publication No. WO 99/59465 and US application No. 2003/0009097. An adhesive construction in accordance with the present invention may replace the adhesive constructions used for attaching these devices to the skin.

In another embodiment of the invention, the adhesive is part of a faecal-collecting device, attaching a bag or another collecting device to the perianal skin.

Experimental
Laboratory Methods
Method 1: Mixing
Premixes of Levamelt and Polar Oil The adhesives were compounded in a Brabender mixer from Brabender OHG, Duisburg, Germany (contains about 60 grams) or a Herrmann Linden LK II 0.5 from Linden Maschinenfabrik, Marienheiden, Germany (contains about 600 grams). The chamber temperature in the mixer was approximately 120° C. and the adhesive was compounded with 50-60 rpm.

Premixtures were made from each polymer. The polymer was added to the mixer and the mixer was started. When the polymer was melted and had a smooth surface, oil was added slowly in small steps, starting with a few ml, followed by increasing amounts. The remaining oil was not added until the first oil was well mixed into the polymer.

For Levamelt/PPO adhesives, the ratio between Levamelt and PPO in the premixture was typically approximately 0.4:0.6

Premixes of Rubber (Styrene Copolymers or Butyl Rubber) and Polyisobutylene.

The rubber was mixed in a 600 g mixer at 150° C., under vacuum until it was a homogeneous mass. Subsequently, polyisobutylene was added. The rubber/polyisobutylene ratio in the premixes was typically approximately 1:1.

Mixing

The premixes, additional oil and polyisobutylene, and hydrocolloids were mixed for 30-60 minutes at 100° C. at 20-30 rpm in a 600 g mixer.

Method 2: Mechanical Degradation of Pre-Cross-Linked Levamelt

In some cases, it was necessary to perform a mechanical degradation of the pre-cross-linked EVA, for example when Levamelt 500 was used. The polymer was mixed for about 10 hours in a cold Hermann Linden LK II 0.5 mixer to get mechanical breakdown of the polymer chains. The heating system was not turned on and the mixing speed was kept low, app. 20 rpm, to ensure optimal mechanical work on the polymer. The breakdown of the polymer was followed by visual inspection of a thermoformed film of the treated polymer. The mechanical treatment was continued until only a minor amount of polymer gel-lumps remained.

Method 3: Gamma Irradiation 1 kilo of the polymer was placed in a plastic bag. The bag was packed and sent to the gamma irradiation supplier, for example BGS Beta-Gamma Service, Wiehl, Germany. The polymer was irradiated with the specified gamma dose, for example 30 kGy. The gamma radiation increases the molar weight of the polymer. When the polymer was returned, it was mixed with oil, to obtain pre-mixtures as described above.

Method 4: Determination of Moisture Absorption

Samples were prepared by thermoformed to an approx. 1±0.1 mm adhesive film between two release liners.

With a punching tool, samples were punched out. Sample size was 25×25 mm. The release liners were removed. The samples were glued to an object glass and placed in a beaker with physiological salt water and placed in an incubator at 37° C.

Calculation:

The sample was weighed over time (=M(10 min)).

For a 25×25 mm sample the area was 6.25 cm² (the surface edges were left out of the area).

The moisture absorption may be calculated as:

$$\text{water abs. after 2 hours} = \frac{M(2 \text{ hours}) - M(\text{start})}{6,25} [g/cm^2]$$

Method 5: Determination of Moisture Vapour Transmission Rate (MVTR)

MVTR was measured in grams per square meter (g/m²) over a 24 hour period using an inverted cup method.

A container or cup that was water and water vapour impermeable having an opening was used. 20 ml saline water (0.9% NaCl in demineralised water) was placed in the container, and the opening was sealed with the test adhesive film. The container was placed into an electrically heated humidity cabinet, and the container or cup was placed upside down such that the water was in contact with the adhesive. The cabinet was maintained at 37° C. and 15% relative humidity (RH). The weight loss of the container was followed as a function of time. The weight loss was due to evaporation of water vapour transmitted through the adhesive film. This difference was used to calculate MVTR. MVTR was calculated as the weight loss per time divided by the area of the opening in the cup (g/m²/24 h). The MVTR of a material was a linear function of the thickness of the material. Thus, when reporting MVTR to characterise a material, it was important to inform the thickness of the tested material. We used 550 μm as a reference. If thinner or thicker samples were measured, the MVTR was reported as corresponding to a 550 μm sample.

Finally, we noted that by using this method, we introduced an error by using a supporting polyurethane (PU) film. The error was eliminated by utilising the fact that the adhesive/film laminate was a system of two resistances in series. When the film and the adhesive were homogeneous, the transmission rate may be expressed as:

$$1/P(\text{measured}) = 1/P(\text{Film}) + 1/P(\text{Adhesive})$$

Hence, by knowing the film permeability and thickness of the adhesive, it was possible to calculate the true permeability of the adhesive (P(Adhesive)) using the following expression:

$$P(\text{adhesive}) = d(\text{Adhesive})/150 \text{ micron} * 1/(1/P(\text{measured}) - 1/P(\text{Film}))$$

where d(Adhesive) was the actual measured thickness of the adhesive and P(Film) was the MVTR of the film with no adhesive, and P(measured) was the actual measured MVTR.

Method 6: Determination of Erosion Resistance

Samples were prepared by thermoforming a 2±0.1 mm adhesive plate between two release liners. Said adhesive plate was transferred and laminated with a non-permeable foil on both sides.

With a punching tool, round samples were punched out and placed in closed beakers with physiological salt water and placed at room temperature (23° C.).

The beakers were rotated to obtain dynamical mechanical stress of the sample at the same time as water absorption took place.

After 24 hours, the eroded part was measured in mm in radial direction from the centre hole towards the outer periphery of the sample.

Method 7: Determination of Peel Failure Mode:

Peel failure mode was determined by peeling the sample from skin.

Peel failure mode, that is adhesive or cohesive failure of the adhesive, was visually observed. Cohesive failure was unwanted, as adhesives with cohesive failure were likely to leave residues on the substrate when removed.

The test samples were prepared by thermoforming an approximately 1±0.1 mm adhesive film between two release liners. Said adhesive film was transfer coated onto a 30 μm polyurethane film.

The test specimens were applied to the underside of the forearm and left for about 2 hours before they were peeled. The results were reported as Adhesive or Cohesive peel failure mode.

Method 8: Dynamic Mechanical Analysis (DMA) and Determination of the Complex Shear Modulus |G*| and tan(δ)

The parameters |G*| and tan(δ) were measured as follows: The adhesives were pressed into a plate of 1 mm thickness. A round sample of 25 mm in diameter was cut out and placed in a RheoStress RS600 rheometer from Thermo Electron. Two plates of 25 mm were placed in parallel and the deformation was fixed at 1% to ensure that measurements were in the linear regime. The measurements were carried out at 32° C.

Materials

| Name | Chemistry | Supplier |
|---|---|---|
| Kraton D 1161 | Styrene block copolymer | Kraton Polymer |
| Oppanol B12 | Polyisobutylene | BASF |
| Levamelt 700 | Ethylene vinyl acetate copolymer | Lanxess |
| Levamelt 500 | Ethylene vinyl acetate copolymer | Lanxess |
| Voranol P2000 | Poly Propylene glycol | Dow Chemical |
| Blanose 9H4XF | Hydrocolloid | Hercules |
| Pektin Pomosin LM 12 | Hydrocolloid | CP Kelco Aps |
| Potato starch | Hydrocolloid | KMC |
| Gelatin | Hydrocolloid | PB Gelatines |

Results

The tables beneath shows examples of adhesive compositions prepared according to the invention.

|  | 77.12 | 77.13 | 77.15 | 77.24 | 77.26 |
|---|---|---|---|---|---|
| Levamelt 500, 15 KGy |  |  | 4 | 6 | 4.3 |
| Levamelt 700, 20 KGY |  | 8 | 4 |  | 4.3 |
| Voranol P 2000 |  | 12 | 12 | 18 | 13 |
| Kristalex F100 |  |  |  |  |  |
| Total % |  | 20 | 20 | 24 | 21.6 |
| Kraton 1161 | 10 | 8 | 8 | 7 | 7.1 |
| Oppanol B12 | 40 | 22 | 22 | 19 | 25.6 |
| Arkon P90 |  |  |  |  |  |
| Total % | 50 | 30 | 30 | 26 | 32.5 |
| Pektin | 10 | 10 | 10 | 10 | 10 |
| CMC | 22.5 | 22.5 | 22.5 | 22.5 | 22.5 |
| Gelatine | 17.5 | 17.5 | 17.5 | 17.5 | 13.1 |
| Total % | 50 | 50 | 50 | 50 | 45.9 |
| Water absorption |  |  |  |  |  |
| 10 min. g/cm$^2$ | 0.08 | 0.08 | 0.08 | 0.10 | 0.10 |
| 60 min. g/cm$^2$ | 0.20 | 0.20 | 0.17 | 0.23 | 0.22 |
| 120 min. g/cm$^2$ | 0.28 | 0.29 | 0.23 | 0.31 | 0.30 |
| Tanδ at 0.01 Hz | 1.2 | 1.0 | 0.8 | 0.76 | 0.85 |
| |G*|, Pa at 1 Hz | $5.6 \times 10^5$ | $3.9 \times 10^5$ | $3.8 \times 10^5$ | $2.8 \times 10^5$ | $3.1 \times 10^5$ |
| Erosion, mm | 1.0 | 0 | 0 | 0 | 0 |
| MVTR, g/m/24 h, 550 μm. | 201 | 1168 | 885 | 1301 | 860 |
| Peel failure mode | adhesive | adhesive | adhesive | adhesive | adhesive |

|  | 77.31 | 77.33 | 77.36 | 77.38 | 77.39 |
|---|---|---|---|---|---|
| Levamelt 500, 15 KGy | 7.8 |  | 6.7 | 7 | 7 |
| Levamelt 700, 20 KGY |  | 6.7 |  |  |  |
| Voranol P 2000 | 21.5 | 18.3 | 18.3 | 20.5 | 20.5 |
| Kristalex F100 |  |  | 8.3 | 4.3 |  |
| Total % | 29.3 | 25 | 33.3 | 31.8 | 27.5 |
| Kraton 1161 | 6.4 | 6.9 | 5.5 | 5.7 | 5.7 |
| Oppanol B12 | 22.9 | 18.1 | 19.5 | 20.1 | 20.1 |
| Arkon P90 |  |  |  | 4.3 | 8.6 |
| Total % | 29.3 | 33.3 | 25 | 30.1 | 34.1 |
| Pektin | 9.8 | 8.3 | 8.3 | 8.6 | 8.6 |

-continued

|  | 77.31 | 77.33 | 77.36 | 77.38 | 77.39 |
|---|---|---|---|---|---|
| CMC | 22 | 22.5 | 18.8 | 19.3 | 19.3 |
| Gelatine | 9.8 | 10.9 | 14.6 | 10.2 | 10.2 |
| Total % Water absorption | 41.6 | 41.7 | 41.7 | 38.1 | 38.1 |
| 10 min. g/cm$^2$ | 0.09 | 0.12 | 0.08 | 0.08 | 0.07 |
| 60 min. g/cm$^2$ | 0.20 | 0.22 | 0.15 | 0.15 | 0.15 |
| 120 min. g/cm$^2$ | 0.27 | 0.30 | 0.21 | 0.22 | 0.20 |
| Tan δ at 0.01 Hz | 0.73 | 0.95 | 0.90 | 0.90 | 0.84 |
| \|G*\|, Pa at 1 Hz | $1.7 \times 10^5$ | $1.0 \times 10^5$ | $1.5 \times 10^5$ | $1.0 \times 10^5$ | $1.0 \times 10^5$ |
| Erosion, mm | 0 | 1.0 | 0 | 0 | 0 |
| MVTR, g/m/24 h, 550 μm. | 1031 | 1332 | 1166 | 1200 | 1106 |
| Peel failure mode | adhesive | cohesive | adhesive | adhesive | adhesive |

77.12 is an example of a composition as described in WO 99/11302. The examples show an increase in the MVTR values by the addition of the polar phase according to the invention. Combining adhesives with high MVTR values with a water vapour permeable backing makes it possible to produce thinner adhesives without compromising the end-users need for a product with a high moist handling capacity.

Compared to 77.12 the addition of the polar phase also lowers the complex shear modulus |G*|. This means that the softness and the tack of the adhesives increases, making the adhesives more adaptable to uneven skin and makes the application procedure of the adhesive less sensitive to human errors. With the exception of composition 77.13 and 15, the examples of the tables have also shown a significant decrease in skin stripping upon removal compared to 77.12, which will increase the end-users skin health.

The addition of the polar phase increases the ratio of the elastic modulus (lower tan δ), however the water absorption levels remains stable, and except for 77.33 the erosion resistance of the adhesive compositions was improved. 77.33 also exhibit cohesive failure mode upon removal. The Levemelt 500-15 KGy is more coherent than Levamelt 700-20 KGy when mixed with Voranol P2000, and the results of 77.33 shows that when utilising higher ratios of the polar oil compared to the polyethylene copolymers, addition of Levamelt 500-15 KGy is needed in order to obtain an adhesive that is suitable for skin applications.

Kristalex F100 is a resin that is predominantly compatible with the polar phase of the adhesive while Arkon P90 is predominantly compatible with the non-polar phase. It is possible as according to the invention to increase the adhesion of either phase by adding phase compatible resins to the composition (77.36, 77.38 and 77.39).

The invention claimed is:

1. A pressure sensitive adhesive composition for skin application comprising:
    10-50% (w/w) based on a total adhesive composition of a polar part;
    10-50% (w/w) based on a total adhesive composition of an apolar part; and
    30-50% (w/w) based on a total adhesive composition of hydrocolloid(s);
    wherein the polar part comprises polar polyethylene copolymer(s) and polypropylene oxide, and the apolar part comprises one of polyisobutylene, styrene block copolymer, and butyl rubber.

2. The pressure sensitive adhesive composition according to claim 1, wherein the polar part comprises polypropylene oxide in a content of above 10% (w/w) of said polar part with a content of the polyethylene copolymer(s) at 10-50% (w/w) of said polar part, and the polar polyethylene copolymer has a melt flow index below 2 g/10 min (190° C./21.1N).

3. The pressure sensitive adhesive composition according to claim 1, wherein the adhesive composition in continuous form exhibits a moisture vapour transmission rate of at least 400 g/m$^2$/24 hours.

4. The pressure sensitive adhesive composition according to claim 1, wherein the polar polyethylene copolymer is selected from the group consisting of ethylene vinyl acetate, ethylene vinyl acetate carbon monoxide, ethylene butyl acetate, ethylene vinyl alcohol, ethylene butyl acrylate, ethylene butyl acrylate carbon monoxide, and combinations thereof.

5. The pressure sensitive adhesive composition according to claim 4, wherein the polar polyethylene copolymer is ethylene vinyl acetate.

6. The pressure sensitive adhesive composition according to claim 5, wherein the ethylene vinyl acetate has a content of 40%-80% (w/w) vinyl acetate.

7. The pressure sensitive adhesive composition according to claim 1, wherein the polar polyethylene copolymer(s) has a molecular weight of above 250,000 g/mol.

8. The pressure sensitive adhesive composition according to claim 1, wherein the polar plasticizing oil is selected from the group of liquid rosin derivatives, aromatic olefin oligomers, vegetable and animal oils and derivatives thereof.

9. The pressure sensitive adhesive composition according to claim 1, wherein a ratio of polar polyethylene copolymer and polypropylene oxide is between 1:1 and 1:4.

10. The pressure sensitive adhesive composition according to claim 1, wherein the composition further comprises a polar polymer with a melt flow index >2 (190° C./21.1N).

11. The pressure sensitive adhesive composition according to claim 1, wherein the composition further comprises a tackifier resin.

12. The pressure sensitive adhesive composition according to claim 1, wherein the composition further comprises an apolar resin compatible with the apolar part of the adhesive.

13. The pressure sensitive adhesive composition according to claim 11, wherein a content of the tackifier resin(s) is 0.1-20% (w/w) of the adhesive composition.

14. The pressure sensitive adhesive composition according to claim 1, wherein the composition further comprises an additional plasticiser selected from the group of mineral oil, citrate oil, paraffin oil, phthalic acid esters, adepic acid esters, liquid resin and solid resin.

15. The pressure sensitive adhesive composition according to claim 1, wherein the composition further comprises a polyethylene wax.

16. The pressure sensitive adhesive composition according to claim 1, wherein the composition further comprised other ingredients selected from the group of antioxidants, stabilisers, fillers, pigments, flow modifiers, and active ingredients.

17. The pressure sensitive paste composition according to claim 1, wherein the polyisobutylene has a molecular weight of below 100,000 g/mol.

18. The pressure sensitive adhesive composition according to claim 1, wherein the styrene block copolymer is a styrene-isoprene-styrene block copolymer.

19. The pressure sensitive adhesive composition according to claim 1, wherein the butyl rubber has an average molecular weight of 200,000 to 600,000 g/mol.

20. The pressure sensitive paste composition according to claim 1, wherein the content of the polar part is 20-40% (w/w) of the total adhesive composition.

21. The pressure sensitive paste composition according to claim 1, wherein the content of the apolar part is 20-40% (w/w) of the total adhesive composition.

22. The pressure sensitive adhesive composition according to claim 1, wherein a ratio of the content of the polar part and the apolar part is between 1:4 and 4:1.

23. A layered adhesive construction comprising a backing layer and at least one layer of the pressure sensitive adhesive composition of claim 1.

24. The layered adhesive construction according to claim 23, wherein the construction further comprises at least one layer of a water absorbing adhesive.

25. The layered adhesive construction according to claim 23, wherein the layer of the pressure sensitive adhesive composition of claim 1 is located for placement between a layer of a water absorbing adhesive and the skin.

26. A medical device comprising a the pressure sensitive adhesive composition of claim 1 and a backing layer.

27. The medical device according to claim 26, wherein the backing layer is non-vapour permeable.

28. The medical device according to claim 26, wherein the backing layer is water vapour permeable and has a moisture vapour transmission rate above 500 g/m$^2$/24 h.

29. The medical device according to claim 26 wherein the medical device is one of a dressing, an ostomy appliance, a prosthesis, e.g. a breast prosthesis, a urine collecting device, a faecal management device, a measuring instrument or a therapeutic instrument, a medical tape, and a bandage.

30. The pressure sensitive adhesive composition according to claim 1, wherein a ratio of the content of the polar part and the apolar part is between 2:3 and 3:2.

* * * * *